United States Patent [19]

Godfrey

[11] 4,227,533
[45] Oct. 14, 1980

[54] FLUSHABLE URINARY CATHETER

[75] Inventor: John C. Godfrey, Syracuse, N.Y.

[73] Assignee: Bristol-Myers Company, New York, N.Y.

[21] Appl. No.: 957,554

[22] Filed: Nov. 3, 1978

[51] Int. Cl.² .................... A61M 25/00; A61M 27/00
[52] U.S. Cl. ........................ 128/349 BV; 128/350 V
[58] Field of Search ............... 128/348, 349 R, 349 B, 128/349 BV, 350 R, 350 V, 351

[56] References Cited

U.S. PATENT DOCUMENTS

| | | | |
|---|---|---|---|
| 274,447 | 3/1883 | Kennish | 128/348 |
| 1,906,678 | 5/1933 | Wappler | 128/348 |
| 2,845,930 | 8/1958 | Brown | 128/348 |
| 3,173,418 | 3/1965 | Boran | 128/349 B |
| 3,331,371 | 7/1967 | Rocchi et al. | 128/349 |
| 3,394,705 | 7/1968 | Abramson | 128/349 |
| 3,583,404 | 6/1971 | McWhorter | 128/240 |
| 3,671,979 | 6/1972 | Moulopoulos | 128/348 |
| 3,726,283 | 4/1973 | Dye et al. | 128/349 BV |
| 3,769,981 | 11/1973 | McWhorter | 128/349 B |
| 3,800,795 | 4/1974 | Walker | 128/275 |
| 3,800,799 | 4/1974 | McWhorter | 128/349 R |
| 3,834,394 | 9/1974 | Hunter et al. | 128/348 |
| 3,848,603 | 11/1974 | Throner | 128/349 R |
| 3,894,540 | 7/1975 | Bonner, Jr. | 128/349 R |
| 3,965,900 | 6/1976 | Boedecker | 128/275 |
| 3,965,910 | 6/1976 | Fischer | 128/349 R |
| 3,981,299 | 9/1976 | Murray | 128/349 B |
| 4,020,840 | 5/1977 | Barsom | 128/276 |
| 4,026,298 | 5/1977 | Gravsz | 128/349 R |
| 4,056,854 | 11/1977 | Boretos et al. | 128/348 |
| 4,140,119 | 2/1979 | Pollack | 128/348 |

FOREIGN PATENT DOCUMENTS

| | | | |
|---|---|---|---|
| 998906 | 10/1976 | Canada | 128/349 B |
| 2447998 | 4/1976 | Fed. Rep. of Germany | 128/349 R |
| 2538709 | 11/1976 | Fed. Rep. of Germany | 128/349 R |
| 733890 | 7/1955 | United Kingdom | 128/349 BV |

OTHER PUBLICATIONS

Detect. Prevent. and Manage. of U.T. Infectious, Calvin Kunin, Sec. Ed. 1974, Pub. Lea & Febiger, pp. 142-195.
Japan Med. News, No. 115, p. 7, 1978, "Urogard System".

*Primary Examiner*—William E. Kamm
*Assistant Examiner*—C. W. Shedd
*Attorney, Agent, or Firm*—Roylance, Abrams, Berdo & Farley

[57] ABSTRACT

A urinary catheter comprising an elongated hollow tube having a proximal end, a distal end, a drainage opening in the distal end and a liquid drainage lumen extending from the opening to the proximal end. A valve is located in the lumen near the distal end. Under normal conditions, the valve is open so as to permit urine to pass from the distal end to the proximal end. However, in response to fluid pressure applied to the valve by a cleansing solution on its side nearest the proximal end, the valve will close off the lumen and prevent access to the distal end. An opening for introducing the cleansing solution into the lumen on the side of the valve nearest the proximal end in an amount sufficient to cause the valve to close and to flush contaminants contained in the lumen out the proximal end is provided.

10 Claims, 10 Drawing Figures

4,227,533

FLUSHABLE URINARY CATHETER

BACKGROUND OF THE INVENTION

1. Field of the Invention

This invention relates to a urinary catheter in which the lumen may be periodically flushed outward to prevent bacterial contamination of the bladder.

2. Description of the Prior Art

The construction and use of catheters for the purpose of periodic or continuous drainage of the urinary bladder is well known in the art. Such devices are useful, for instance, when the urethra is blocked for any reason, causing retention of urine; when voluntary voiding is inadequate; when voluntary control of the sphinchter has been lost due to trauma, neurological damage or surgery; when involuntary emptying of the bladder is desired to facilitate diagnostic or surgical procedures; or for a variety of other reasons.

A large variety of urinary catheters is known. These include simple tubes, tubes with expandable tips, and the Foley catheter which combines the advantages of the first two and is therefore the most popular for continuous catheterization beyond about 24 hours. In its simplest form, the Foley catheter consists of a flexible (rubber or plastic) tube of about 4–7 mm. diameter which is fabricated with a small diameter tube integral with the wall and leading to an expandable "balloon" chamber which is just below the tip which will drain the bladder. The chamber is collapsed for ease of insertion and once in place it is expanded with sterile medium such as air or saline solution to prevent the catheter from slipping out through the urethra.

The most common and troublesome complication of urinary catheterization is colonization of the bladder and eventually the entire urinary tract with pathogenic bacteria, yeast and/or fungi. It has been reported that even with the best of available equipment and sterile technique, more than 25% of patients with indwelling urinary catheters can be expected to develop urinary tract infections after 30 days of continuous catheter drainage. Many attempts have been made to overcome this problem. Prophylactic use of systemic antibiotics which are excreted in the urine has not been successful since colonization is only slightly delayed and occurs with organisms resistant to the antibiotics used. Bladder irrigation with a solution of 0.25% acetic acid or a solution of neomycin-polymyxin is moderately successful, but requires a large amount of extra nursing attention. When this method is used, it is usually done with a triple-lumen Foley catheter as shown in FIG. 44 in a text by Calvin M. Kunin entitled "Detection, Prevention and Management of Urinary Tract Infections", Lea & Febiger, Philadelphia, Pa., 1974, 2d-edition, Section IV, entitled "Care of the Urinary Catheter".

The most common route of infection, once the closed drainage catheter has been placed using sterile technique, is colonization of the receiving bag, followed by retrograde ascent of the pathogens up the lumen of the catheter. In view of the non-motile nature of the pathogens, this occurrence was somewhat of a mystery until the early 1960's when careful observations revealed that small bubbles form along the walls of the catheter tubing and that over a period of hours, these bubbles grow and eventually separate from the wall and rise. The associated turbulent flow in the opposite direction of a slowly descending stream of urine eventually carries the organisms all the way to the bladder. The emplacement of a bubble trap in the line merely delays the process by a day or two, as the trap becomes infected and the process is repeated above it.

SUMMARY OF THE INVENTION

The present invention provides a urinary catheter comprising an elongated hollow tube having a proximal end, a distal end, a drainage opening in the distal end and a liquid drainage lumen extending from the opening to the proximal end. A blocking means, e.g., a valve, is located in the lumen near the distal end. Under normal conditions, the valve is open so as to permit urine to pass from the distal end to the proximal end. However, in response to fluid pressure applied to the valve by a cleansing solution on its side nearest the proximal end, the valve will close off the lumen and prevent access to the distal end. A means for introducing the cleansing solution into the lumen on the side of the valve nearest the proximal end in an amount sufficient to cause the valve to close and to flush contaminants contained in the lumen out the proximal end is provided.

DESCRIPTION OF THE PREFERRED EMBODIMENTS

Figure 1:
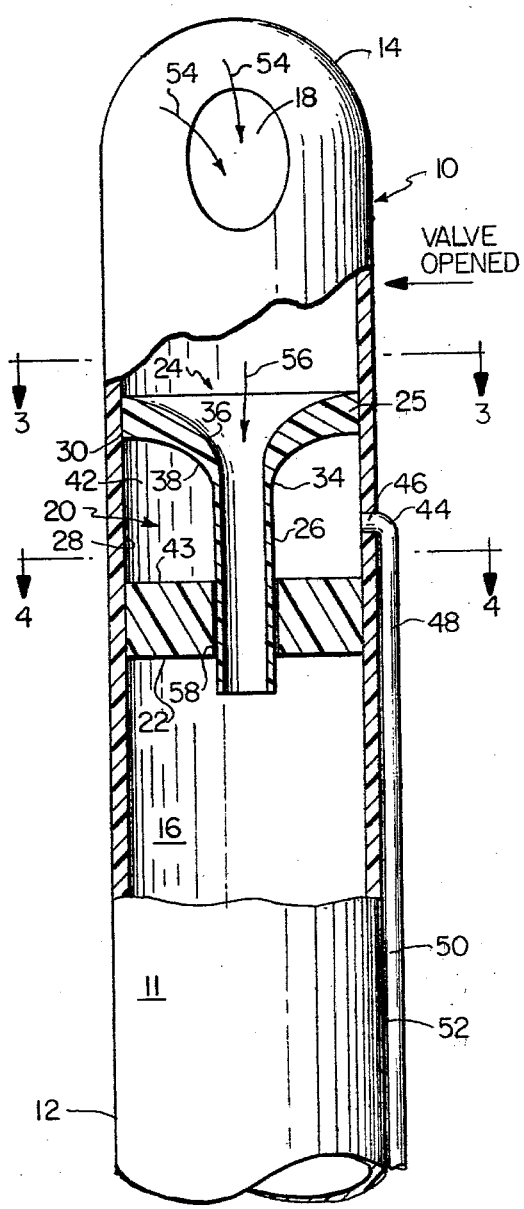
FIG. 1 is a view of the distal end of the flushable urinary catheter taken in the longitudinal plane and showing a cutaway portion in cross-section, the view shown with the valve in the open position.

The particular device set forth in the following description is a catheter for collecting urine from bladders which includes an automatic non-mechanical valve which operates during the flushing mode to prevent any re-entry of any voided urine or the flushing solution into the bladder. Thus, if desired, a strong chemical bacteriacide may be incorporated into the flushing solution.

Although the flushable urinary catheter of this invention can be used with the human body in any position, i.e., standing up or lying down, the drawings show the device as it would be used with the human body standing up. Reference to upper and lower surfaces therefore refer to surfaces as viewed in the drawings with the flushable urinary catheter in the upright or vertical position.

Referring now to FIG. 1, there is shown a catheter 10 comprising an elongated hollow tube having a proximal end 12 and a distal end 14. A liquid drainage lumen 16 extends from the distal end 14 to the proximal end 12. There is an opening or inlet port 18 in the distal end 14 which in the normal mode delivers urine from the bladder into the lumen 16 of the catheter 10.

Located at the distal end of the catheter 10 adjacent to the downstream side of the inlet port 18 is a valve shown generally as 20. The valve is comprised of a retaining member or valve body 22, a funnel shaped, or first portion, 24 including a sleeve, or second portion, 26 and incorporates the sidewall 28 of the catheter tube 11. The outer periphery of the large end of the cone shaped portion 25 of the funnel 24 is attached at 30 to the inner surface of the walls of the catheter tube 11 to assure a fluid-tight joint between the two surfaces. The funnel 24 includes a flexible sleeve 26 attached at 34 to the small end of cone 25. In the preferred embodiment, the funnel 24 is fabricated as a single component, but it may be fabricated from a cone 25 and a flexible sleeve 26 secured at a fluid-tight joint 34. The wall thickness of the cone 25 tapers from a thick portion at the point of attachment 30 to a relatively thin portion at the point of attachment 34 to the sleeve 26. In between the two points of attachment of the cone 25, the upper and lower surfaces 36 and 38, respectively, are gracefully shaped into gentle curves. The length and flexibility of the sleeve 26 will be discussed hereinafter.

Figure 2:
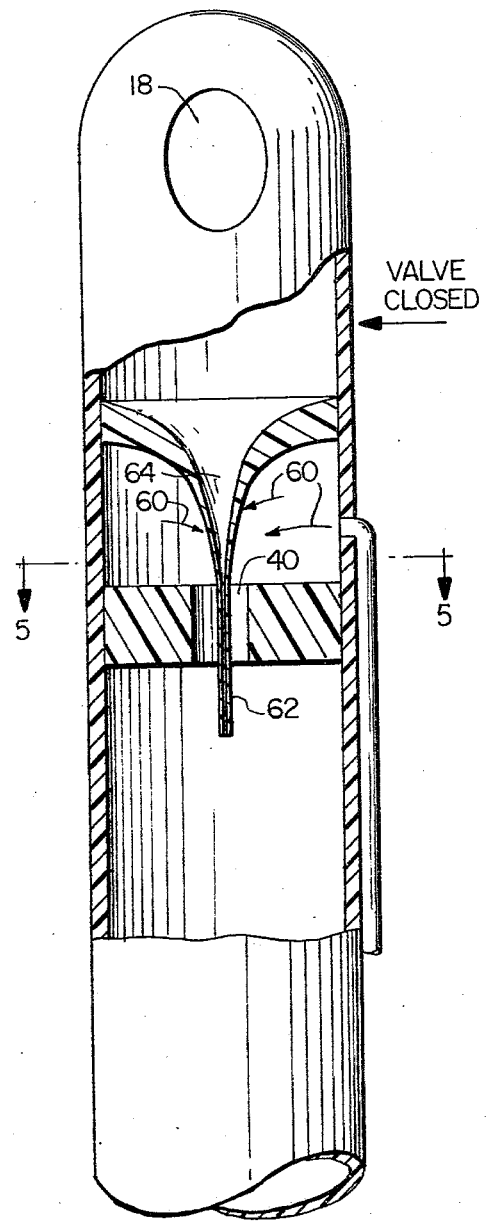
FIG. 2 is a view similar to FIG. 1 with the valve shown in the closed position.

The retaining member 22 is a right circular cylinder with a coaxial bore 40 (see FIG. 2) having the circular sidewall of the bore parallel with the longitudinal axis of the inner sidewalls of the catheter tube 11. The retaining member 22 is located at the distal end of the catheter and on the downstream side of the funnel member 24 and is secured to the inner wall 28 of the catheter 11 by fluid-tight attaching means. The exact location of the retaining member 22 is not critical but it is positioned so that a chamber 42 is formed between the upper surface 43 of the retaining member 22 and the lower surface 38 of the funnel 24. In addition, the position of the retaining member 22 and the length of the flexible tube 26 must be such that the flexible tube extends through the bore 40 of the retaining member 22.

All of the components of the valve 20 shown in this embodiment are symmetrical about the longitudinal axis of the catheter.

A side port opening 46 in the side wall of the catheter tube 11 is located approximately midway between the funnel member 24 and the retaining means 22. Attached to the outer side wall of the catheter tube 11 and running in a longitudinal direction parallel to the catheter tube 11 is a flushing tube 44 for carrying flushing solution from the proximal end of the catheter to the valve chamber 42. The tube 44 has a passageway 48 running the full length of the catheter and has a right angle bend at the port 46 so that the center passageway of the tube is in axial alignment with the center of port 46. The tube 44 is secured to the outer sidewall of the catheter tube 11 to provide a fluid-tight joint around the port 46 and is also secured either continuously along its length or at selected fastening points as at 50 and 52 to the sidewall of the catheter tube 11. Alternatively, a passageway may be formed into the sidewall of the catheter tube 11. In either case, the fabrication must assure a flowpath from the proximate end of the catheter to the chamber 42 of the valve 20.

The operation of the flushable urinary catheter is described starting with the valve in the open position enabling urine to flow into one or more ports 18 in a direction shown by arrows 54 of FIG. 1 through the passageway at the distal end of the catheter tube 11 and into the mouth of the funnel 24 of the valve 20 as shown by the arrow 56. From the funnel mouth, the urine passes through the funnel 24 into and through the sleeve 26. The gentle pressure of the urine on the inner sidewalls of the flexible sleeve 26 keeps the sleeve cylindrical in shape, thus permitting the urine to flow through the sleeve into the open portion of the lumen 16 through which it flows to the proximate end.

As the flexible sleeve 26 expands, it may or may not come in contact with the inner sidewalls 58 which form the bore or passageway 40 in the retaining means 22. When contact is made between the outer walls of the sleeve 26 and the inner walls 58 of the retaining means 22, the passageway between the lumen 16 and the chamber 42 is closed, thus preventing urine from entering the chamber or flushing tube 48 through port 46. If contact is not made between the outer walls of the sleeve 26 and the inner walls 58 of the retracting means 22, retrograde flow of urine through the chamber 42 back down the tube 48 may be prevented by one or more check valves and/or by the resting piston in the pump used to deliver flushing solution. Such piston and associated valves do not form a part of this invention and are not shown.

When it is desired to flush the lumen 16 of the catheter tube 11, the flushing solution is applied at the proximate end of the flushing tube 48 from where it flows through the passageway 48 of the tube, through the port 46 and into the chamber 42 of the catheter 10. The direction of flow is shown by the arrows 60 in FIG. 2. The pressure of the flushing solution on the flexible sidewalls of the sleeve 26 causes the sleeve to collapse as at 62 of FIG. 2, closing the valve, and thus sealing the passageway 64. This prevents flow of the flushing solution from chamber 24 through the sleeve 26 and into the bladder. When the flow of the flushing solution is discontinued at the source, the pressure from the solution on the sides of the flexible sleeve ends. The sleeve 26 then either expands to its cylindrical shape by its own elastic nature or returns to its cylindrical shape as soon as the flow of urine exerts an internal pressure on the sidewalls to produce the same effect. In either case, the valve opens automatically when the flow of flushing solution is discontinued at the source.

The tube 48 may be in communication with a syringe pump or the like, not shown, which would operate intermittently, as for instance controlled by an automatic timing device, to deliver a fixed amount of solution on a pre-determined schedule. The amount of flush solution and the time of its delivery would depend upon the observed rate of bubble formation, but with experience it will be possible to define reasonable limits, e.g., 10 ml. of flush solution in 1 minute every 20 minutes, 30 minutes, hour, etc.

Figure 3:
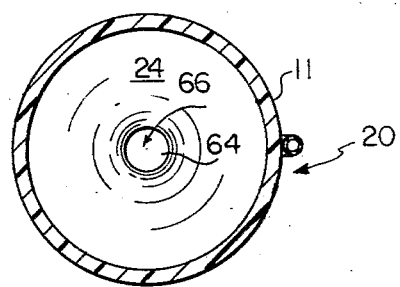
FIG. 3 is a cross-sectional view taken in a transverse plane from the distal end along lines 3—3 of FIG. 1 with the valve shown in the open position.

FIG. 3 shows the passageway 64 through the funnel 24 with the valve 20 open as it appears looking down from the distal end of the catheter in cross-section. The arrow 66 represents the downward flow of urine through the passageway.

Figure 4:
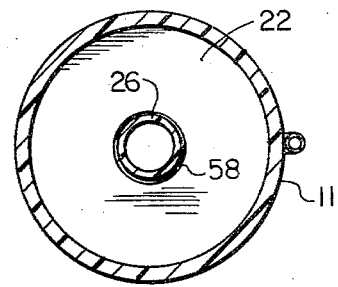
FIG. 4 is a cross-sectional view taken in a transverse plane from the distal end along lines 4—4 of FIG. 1 with the valve shown in the open position.
Figure 5:
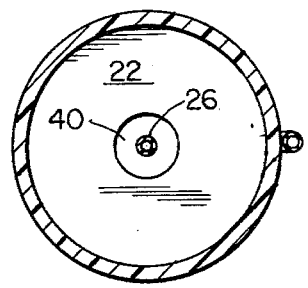
FIG. 5 is a cross-sectional view taken in a transverse plane from the distal end along lines 5—5 of FIG. 2 with the valve shown in the closed position.

FIG. 4 shows the inner structure of the valve in the open position with the sleeve 26 in contact with the inner walls of the retaining means 22.

FIG. 3 also shows the inner structure of the valve and catheter in cross-section with the valve as it appears in the closed position. The sleeve 26 is collapsed and the flushing solution flows through the bore 40 of the valve body 22 into the drainage lumen 60.

Figure 9:
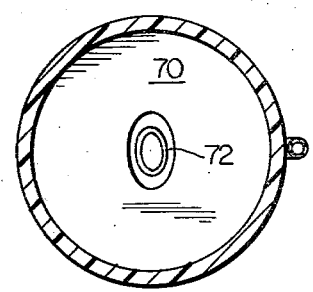
FIG. 9 is a cross-sectional view in a transverse plane taken from the distal end along lines 9—9 of FIG. 8.
Figure 10:
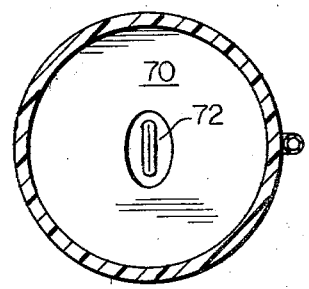
FIG. 10 is a cross-sectional view in a transverse plane taken from the distal end and taken along lines 10—10 of FIG. 6.

FIGS. 6–10 show a second embodiment of the urinary catheter of this invention. As described in relation to the first embodiment, the valve 69 of the second embodiment is comprised of a retaining member 70 and a funnel member 72 which in cooperation with the inner sidewalls 28 of the catheter hollow tube 11 forms a valve chamber 76. In this second embodiment, the passageway 78 through retaining member 70, as it appears in transverse section, is oval shaped as best seen in FIGS. 9 and 10. The passageway 78, as seen in cross-section in FIG. 7, for example, is formed with the sidewalls 80 gently curved from the large opening 82 at the inlet side of the retaining member 70 to the small opening 84 at the discharge side.

Figures 6, 7, 8:
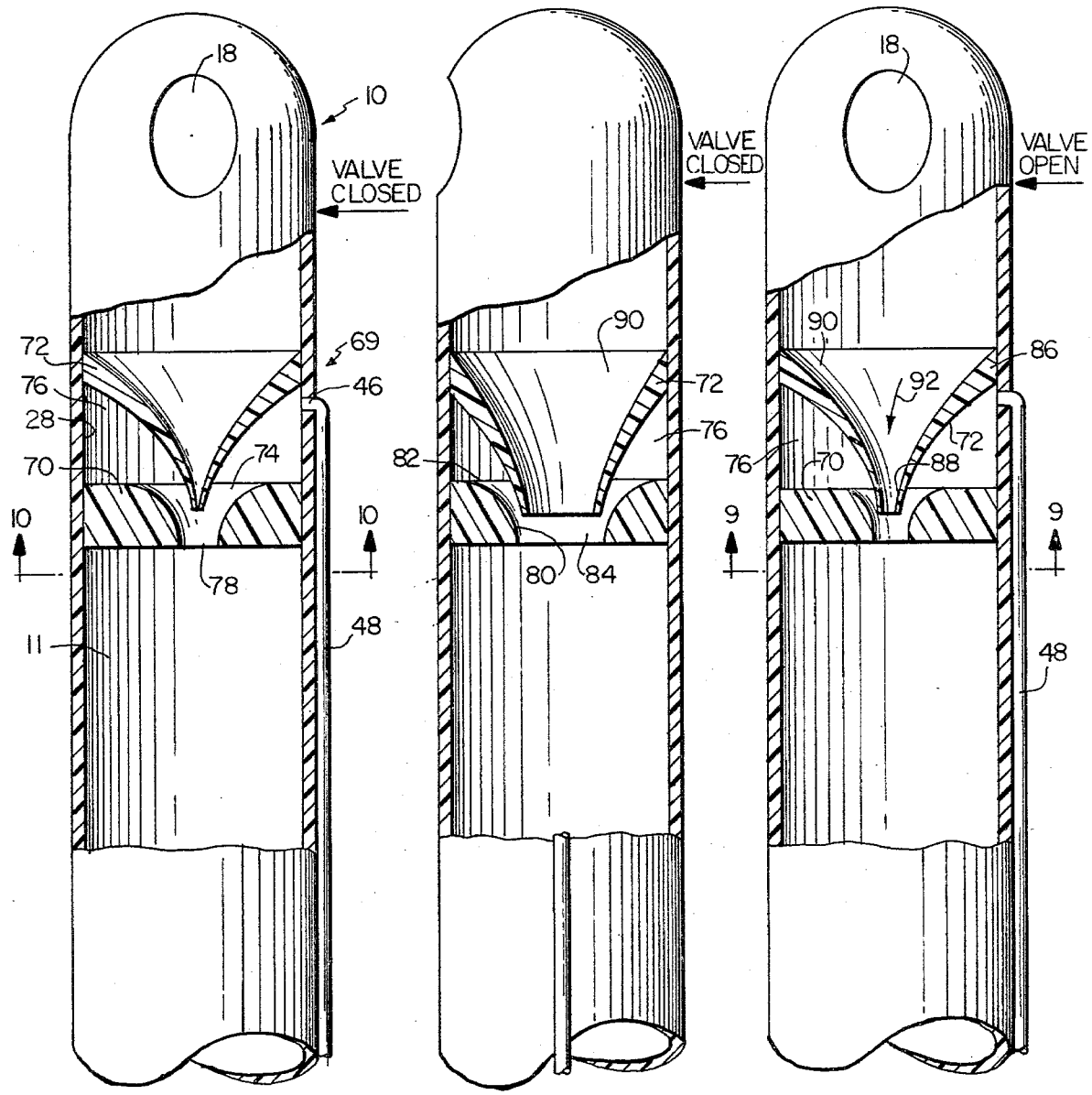
FIG. 6 is a view of the second embodiment of the distal end of a flushable urinary catheter taken in a longitudinal plane and showing a cutaway portion in cross-section, the view taken of the catheter with the valve shown in the closed position.
FIG. 7 is similar to FIG. 6 with the catheter rotated 90° about its longitudinal axis with respect to the view shown in FIG. 6.
FIG. 8 is a view similar to FIG. 6 with the valve shown in the open position.

The funnel member 72 has an oval shaped transverse cross-section as best seen in FIG. 9. The funnel member 72 has oval shaped upper and lower openings and is formed with the sidewalls, as viewed in longitudinal cross-section as seen in FIGS. 6–8, for example, tapered from the upper opening to the lower opening. That is, the sidewalls are generally thick and inflexible as at 86 at the upper opening and relatively thin as at 88 of the lower opening.

As with the first embodiment, the longitudinal position of the retaining member 70 and the funnel member 72 are not critical. However, the funnel member must be located adjacent to the inlet port 18 and on the distal end side of the flushing solution side port 46. The longitudinal position of the retaining member 70 must be on the proximate side of the side port 46 and its longitudinal position must be such that the end of the thin flexible funnel as at 88 is located substantially at the center of the passageway through the retaining member 70 as seen in FIG. 8.

The interaction of the funnel member 72 with the retaining member 70 during the two modes of operation of the valve is described together with the operation of the catheter hereinafter.

Urine flows through the inlet port 18 into the inner tubular portion of the catheter to the large opening 90 of funnel member 72 from where it flows through the smaller opening downwardly through the center passageway of the retaining member 70 into the lower tubular portion of the catheter and outwardly through the proximate end of the catheter. The flow of urine is shown by the direction of arrow 92 in FIG. 8. During the time the urine is flowing through the open valve 69, the thin tapered flexible ends of the funnel as shown at 88 have come in contact with the sidewalls of the oval shaped opening in the retaining member 70. This contact of the portion 88 of the funnel with the sidewalls of the retaining member 70 prevents urine from flowing into the valve chamber 76 and through side port 46 into the flushing solution tube 48. When it is desired to flush the lumen of the flushable urinary catheter, a flushing solution is applied to the proximate end of the flushing solution tube 48 causing it to flow through side port 46 into valve chamber 76. The pressure of the flushing solution in chamber 76 upon the sidewalls of the funnel member 72 causes the sidewalls of the funnel to pull away from the sidewalls of the retaining member 70, thus leaving a passageway 74 for the flushing solution to enter and decontaminate the inner sidewalls of the flushable urinary catheter 16. The valve is shown in this closed position in FIGS. 6 and 7.

Typical materials which may be used in making the valve include synthetic rubbers, silicone rubber, soft polyethylene, polyvinylchloride, Silastic ® and the like.

The catheter of this invention, especially with the addition of the automatic pump, has several advantages, including the following:

1. Retrograde movement of bubbles and microorganisms is effectively suppressed.
2. There are no mechanical moving parts within the catheter itself, reducing the probability of failure in use.
3. The flushing solution may contain a powerful antiseptic if desired, without exposing the patient to such agent.
4. Convenience in emplacement and the need for minimal surveillance by the nursing staff will make this device highly acceptable in the profession.
5. The expected remarkable decrease in catheter-borne urinary tract infections in patients requiring long-term catheterization will render this a very attractive device.

Although the operation of the invention has been described in relation to two specific embodiments, it is apparent that variations may be made in the specific embodiments without departing from the invention as claimed. For example, it will be recognized that the catheter of this invention may be constructed with the addition of the standard Foley "balloon", either above, coincident with, or below the level of the flush valve mechanism.

I claim:

1. A urinary catheter comprising an elongated hollow tube having a proximal end, a closed distal end, a drainage port in said distal end, a liquid drainage lumen extending from said port to said proximal end, blocking means located in said lumen near said distal end which under normal conditions will permit urine to pass from said distal end to said proximal end, but which in response to fluid pressure applied on the side of said blocking means nearest said proximal end by a cleansing solution will close off the lumen and prevent fluid flow to or from said distal end, said blocking means being a valve which comprises in combination, (a) a funnel shaped member including a large opening in communication with a small opening, the large opening being sealably engaged with the wall of said drainage lumen and located nearest said drainage port, and a passage connecting said openings, said passage extending in the direction of the longitudinal axis of said lumen, the walls of said passage nearest said small opening being more flexible than the wall nearest said large opening wherein the wall thickness of said passageway tapers from a thick portion at the point of engagement with said drainage lumen to a thinner portion at said small opening, and (b) a retaining means spaced apart from the large opening of said funnel shaped member in the direction of said proximal end, said retaining means comprising a solid portion which closes off a portion of said lumen and including an opening, such that the walls of said opening may be in contact with at least a portion of the flexible wall of said passage to permit urine to pass therethrough, whereby a chamber is formed between said funnel shaped member and said retaining means, and means for introducing a cleansing solution into said lumen on the side of said blocking means nearest said proximal end in an amount sufficient to cause said blocking means to close and to flush contaminants out said proximal end, said introducing means comprising an opening in the sidewall of said lumen located between said funnel shaped means and said retaining means, said opening being in communication with a tube which extends from said opening towards said proximal end.

2. A catheter as defined in claim 1, wherein a portion of the flexible walls of said passage extend through the opening in said retaining means.

3. A catheter as defined in claim 1, wherein the opening in said retaining means and the passgeway in said funnel shaped member are circular in cross-section.

4. A catheter as defined in claim 1, wherein the opening in said retaining means and the passageway in said funnel shaped member are oval in cross-section.

5. A flushable urinary catheter comprising:
a tube having a closed distal end and an open proximal end, said distal end adapted to be received in the patient's bladder;
a urine inlet port through said tube adjacent said distal end;
means defining a pressure chamber in said tube between said urine inlet port and said proximal end;
fluid pressure responsive valve means located in said pressure chamber for permitting urine flow from said urine inlet port through said tube toward said proximal end when open and for blocking off fluid flow in said tube between said urine inlet port and said valve means when closed;
means, coupled to said tube, for introducing a flushing fluid under pressure into said pressure chamber and for closing said valve means,
said means for introducing and closing including
a flushing fluid conducting member extending from said proximal end to said pressure chamber, and
a flushing fluid port at the end of said flushing fluid conducting member communicating with said pressure chamber for introducing the flushing fluid into said pressure chamber,
said pressure chamber having an orifice allowing the flushing fluid therein to flow therefrom toward said proximal end,
whereby the flushing fluid introduced into said pressure chamber closes said valve means preventing backflow thereof towards said urine inlet port, exits said pressure chamber via said orifice, and flows down said tube towards said proximal end, thereby flushing the interior of said tube.

6. A flushable urinary catheter according to claim 5, wherein said valve means comprises an elongated, open-ended hollow member having a first portion secured to the interior of said tube and a second portion partially received in said orifice.

7. A flushable urinary catheter according to claim 6, wherein said second portion is circular in cross-section.

8. A flushable urinary catheter according to claim 6, wherein said second portion is oval in cross-section.

9. A flushable urinary catheter according to claim 6, wherein said first portion is funnel-shaped.

10. A flushable urinary catheter according to claim 6, wherein said valve means hollow member is in the form of a tube, said second portion thereof being more flexible than said first portion thereof.

* * * * *